(12) United States Patent
Tanikawa et al.

(10) Patent No.: US 7,801,589 B2
(45) Date of Patent: Sep. 21, 2010

(54) IN-VIVO EXAMINATION METHOD AND IN-VIVO EXAMINATION APPARATUS

(75) Inventors: Yoshihisa Tanikawa, Tokyo (JP); Tadashi Hirata, Hachioji (JP); Yasuaki Natori, Hachioji (JP); Chika Nakajima, Chofu (JP); Yoshihiro Kawano, Fuchu (JP)

(73) Assignee: Olympus Corporation, Tokyo (JP)

( * ) Notice: Subject to any disclaimer, the term of this patent is extended or adjusted under 35 U.S.C. 154(b) by 692 days.

(21) Appl. No.: 11/640,921

(22) Filed: Dec. 19, 2006

(65) Prior Publication Data

US 2007/0167842 A1 Jul. 19, 2007

(30) Foreign Application Priority Data

Dec. 22, 2005 (JP) ............................. 2005-369763
Feb. 23, 2006 (JP) ............................. 2006-046625

(51) Int. Cl.
*A61B 6/00* (2006.01)
(52) U.S. Cl. ...................... 600/476; 600/407; 600/436; 600/475
(58) Field of Classification Search ................ 600/407, 600/436, 475, 476
See application file for complete search history.

(56) References Cited

U.S. PATENT DOCUMENTS 6,161,035 A * 12/2000 Furusawa ................... 600/476
6,400,501 B2 * 6/2002 Tsuchiya et al. ............ 359/380
6,414,805 B1 * 7/2002 Reichman et al. ........... 359/889
6,600,943 B1 * 7/2003 Kiuchi et al. ................ 600/407
6,636,755 B2 * 10/2003 Toida ......................... 600/407
6,687,534 B2 * 2/2004 Tsujita ........................ 600/476
2005/0059894 A1 3/2005 Zeng et al.
2005/0200947 A1 9/2005 Hirata et al.

FOREIGN PATENT DOCUMENTS

| EP | 1731941 A1 | 12/2006 |
|---|---|---|
| JP | 2000-262460 | 9/2000 |
| JP | 2004-519488 | 6/2004 |
| JP | 2004070140 | 3/2005 |
| JP | 2005-241671 | 9/2005 |
| WO | WO 02/064084 A2 | 8/2002 |
| WO | 2005096059 A1 | 10/2005 |

OTHER PUBLICATIONS

Extended European Search Report dated Sep. 5, 2007 for EP Application No. 06026442.1.

* cited by examiner

*Primary Examiner*—Brian Casler
*Assistant Examiner*—Baisakhi Roy
(74) *Attorney, Agent, or Firm*—Pillsbury Winthrop Shaw Pittman, LLP

(57) ABSTRACT

An object is to easily and reliably reach an examination site. The present invention provides an examination method of carrying out in-vivo examination using an in-vivo examination apparatus capable of fluorescence examination and reflected-light examination and includes the steps of setting a reference position so as to set an examination site by carrying out reflected-light examination, switching from reflected-light examination to fluorescence examination, and moving from the reference position to the examination site.

5 Claims, 13 Drawing Sheets

IN-VIVO EXAMINATION METHOD AND IN-VIVO EXAMINATION APPARATUS

BACKGROUND OF THE INVENTION

1. Field of the Invention

The present invention relates to an in-vivo examination method and an in-vivo examination apparatus that allow in-vivo examination of tissue of a living organism.

The present invention also relates to an objective lens, a microscope apparatus, and a microscopy method.

This application is based on Japanese Patent Applications, Nos. 2005-369763 and 2006-046625, the contents of which are incorporated herein by reference.

2. Description of Related Art

Conventionally, in-vivo examination of tissue of a living organism has been carried out by making a large incision in the organism to expose the site to be examined or by excising tissue including the site to be examined.

In particular, for brain examination, an apparatus and method for examining brain tissue by thinning the cranial bone and employing multiphoton excitation {are used (for example, refer to Japanese Translation of PCT International Application, Publication No. 2004-518488).

A technology for carrying out fluoroscopy on the brain of a living organism by using an optical fiber, instead of an objective optical system, is also known (for example, refer to Japanese Unexamined Patent Application, Publication No. 2000-262460).

When carrying out such examinations, for example, mouse-brain researchers specializing in central nervous system pharmacology or neurophysiology carry out experiments by locating regions in the actual brain tissue on the basis of data about the tissue and anatomy of small laboratory animals, such as mice, arranged into an atlas.

However, when a large incision is made in an organism for examination, there is a problem in that the condition of an organism in which an incision is made differs from the condition of an organism in which no incision is made. Furthermore, when tissue is excised for examination, there is a problem is that the organism cannot be examined in vivo.

There is also a problem in the examination method disclosed in Japanese Translation of PCT International Application, Publication No. 2004-518488 in that tissue in deep regions of the brain cannot be examined.

According to the examination method disclosed in Japanese Unexamined Patent Application, Publication No. 2000-262460, an examination site is determined only on the basis of a detected fluorescence image of a specific fluorochrome-labeled site. Thus, the general location of the examination site can be detected, but it is difficult to determine whether or not the detected area is the actual site desired to be examined. Furthermore, depending on the position and direction of insertion of the optical fiber, there is a possibility that the site to be examined cannot be reached. In some cases, the optical fiber may pass through the examination site and damage the tissue at the examination site.

A microscope system suitable for in-vivo examination of animals is known (for example, refer to Japanese Unexamined Patent Application, Publication No. 2005-241671).

This microscope system includes an objective lens having a small-diameter end section that can be inserted into the body of an animal in a less invasive manner. The microscope system employs a confocal microscopy method in which the end surface of the objective lens is positioned close to or pressed against the examination site in the body of the animal and excitation light, such as laser light, is emitted, and the fluorescence that returns from the examination site is observed.

In such a microscope system, the examination site has be to positioned extremely close to the end surface of the objective lens because the working distance of an objective lens having a small-diameter end section is extremely small, i.e., several hundred micrometers, and the depth of field is extremely shallow because it employs a confocal microscope. Therefore, when the examination site can be positioned sufficiently close to the end surface of the objective, a clear fluorescence image can be acquired.

However, when such a microscope system is used for examination of a lumen, the following problems occur.

In other words, when the small-diameter end section of the objective lens is inserted into a lumen of a laboratory animal, the tip of the small-diameter end section is positioned in the hollow space of the lumen and is not positioned close to the inner wall of the lumen. Therefore, it is difficult to focus at the examination site, such as a tumor formed on the inner wall of the lumen.

In such a case, if the examination site is relatively soft, the lumen in the laboratory animal's body can be deformed by applying external pressure to the animal's body so as to move the inner wall of the lumen closer to the tip of the small-diameter end section. However, when the lumen is positioned deep inside the body, it is difficult to apply pressure to the lumen. In addition, even when the examination site is temporarily or unintentionally focused, it is difficult to stably maintain the focused state for a long period of time.

BRIEF SUMMARY OF THE INVENTION

An object of the present invention is to provide an in-vivo examination method and an in-vivo examination apparatus for easily and reliably reaching an examination site without unnecessarily damaging a living organism.

Another object of the present invention is to provide an objective lens, a microscope apparatus, and a microscopy method that are capable of clearly and stably examining an examination site positioned on the wall surface of a lumen inside the body of a living organism, such as a small laboratory animal.

To achieve the above-described object, the present invention includes the following solutions.

A first aspect of the present invention provides an examination method of carrying out in-vivo examination using an in-vivo examination apparatus capable of fluorescence examination and reflected-light examination, the method including the steps of defining a reference position for setting an examination site by carrying out reflected-light examination; switching from reflected-light examination to fluorescence examination; and moving from the reference position to the examination site.

This aspect may include a step of automatically detecting a focal position.

The aspect may also include a step of automatically detecting the examination site from an acquired image and a step of moving to the examination site on the basis of in-vivo information.

A second aspect of the present invention provides an in-vivo examination apparatus including an orientation changing mechanism; a control device configured to control the operation of the orientation changing mechanism; a switching device configured to switch between reflected-light examination and fluorescence examination; a reference-position defining unit configured to define a reference position so as to set an examination site by carrying out reflected-light examination; and an examination-site setting unit configured to set the examination site.

With this aspect the orientation changing mechanism may include a vertical-direction driving mechanism configured to move a focusing unit or a specimen table in an optical axis direction, a horizontal-direction driving mechanism configured to move the focusing unit or the specimen table in a direction orthogonal to the optical axis direction, and a rotational-direction driving mechanism configured to rotate the optical axis, and the control device may control at least the vertical-direction driving mechanism among the driving mechanisms.

The aspect may also include a focal-position automatic detection mechanism configured to automatically detect a focal position and an examination-site detection mechanism configured to automatically detect the examination site from an acquired image.

With this aspect the control device may include an in-vivo information storing unit configured to store in-vivo information and an examination-site setting unit configured to read out the in-vivo information stored in the in-vivo information storing unit and set the examination site on the basis of the read out in-vivo information.

The first and second aspects of the present invention are advantageous in that the examination site can be easily and reliably reached without unnecessarily damaging the living organism.

A third aspect of the present invention provides an objective lens including a small-diameter end section that can be inserted into a body lumen, a deflecting member configured to deflects the optical axis in a direction intersecting with the longitudinal axis so that the focal point is disposed outward of the small-diameter end section in the radial direction, and focal-position adjusting means for displacing the position of the focal point in the radial direction.

According to this aspect, by inserting the small-diameter end section into the body lumen, the outer peripheral surface of the small-diameter end section is disposed close to the inner wall surface of the body lumen. Light that is transmitted along the optical axis that extends in the longitudinal-axis direction of the small-diameter end section is deflected by the deflecting member in a direction orthogonal to the longitudinal axis and is directed outward in the radial direction. Then, the inner wall surface of the body lumen positioned close to the outer peripheral surface of the small-diameter end section is focused. Thus, even when the working distance and the depth of field are small, a clear image of the inner wall surface of the body lumen can be constantly acquired.

In this aspect, the focal-position adjusting means may carry out focal-point adjustment by changing the focal length of a lens. In the above-described aspect, the focal-position adjusting means may include a liquid lens.

In this way, the size of the objective lens may be reduced.

This aspect may include a transparent member that is disposed at least in the vicinity of the focal position, outward of the small-diameter end section in the radial direction.

In this way, examination can be easily carried out by pressing the transparent member against the inner wall surface and flattening the inner wall surface. Furthermore, the inner wall surface of the body lumen can be more reliably positioned close to the focal position, and more stable images can be acquired.

In this aspect, the focal-position adjusting means may be interposed between the transparent member and the small-diameter end section and may include an actuator that changes the distance therebetween.

In this way, even when the working distance is constant, the focal position can be easily adjusted by operating the actuator so as to adjust the distance between the transparent member and the small-diameter end section.

This aspect may include fixing means, disposed in the periphery of the small-diameter end section, for fixing the small-diameter end section to the surface of the body lumen wall.

In this way, more stable examination can be carried out because, by operating the fixing means, the small-diameter end section can be fixed to the surface of the body lumen wall.

In this aspect, the fixing means may be constituted of a balloon.

In this way, the small-diameter end section can be easily fixed to the body lumen by inflating the balloon that is disposed around the small-diameter end section and by pressing the surface of the body lumen wall in a manner such as to push the wall outward.

In this aspect, it is preferable that the balloon be divided into a plurality of sections in the circumferential direction and each section be independently inflatable or deflatable.

In this way, the focal position can be moved while supporting the small-diameter end section with respect to the body lumen by changing the inflation and deflation state of the balloon in the circumferential direction. In particular, by inflating or deflating the balloon that is disposed on the optical axis including the focal position, the focal position can be moved in the radial direction.

This aspect may include a rotating mechanism that rotates the deflecting member around the longitudinal axis of the small-diameter end section.

In this way, an examination range around the circumferential direction can be examined by operating the rotating mechanism so as to rotate the deflecting member around the longitudinal axis and move the focal position in the circumferential direction of the body lumen.

In this aspect, the deflecting member may be constituted of a conic mirror.

In this way, an examination range around the circumferential direction can be examined without rotating the deflecting member.

A fourth embodiment of the present invention provides a microscope apparatus including a light source; an optical scanning unit configured to two-dimensionally scan light from the light source; an objective lens configured to irradiate a body lumen with the light scanned by the optical scanning unit and collect return light from the body lumen; and an optical detector configured to detect the return light collected by the objective lens and transmitted through the optical scanning unit. The objective lens includes a small-diameter end section that is inserted into the body lumen and a deflecting member that deflects the optical axis in a direction intersecting with the longitudinal axis so that the focal point is disposed outward of the small-diameter end section in the radial direction. The microscope apparatus includes focal-position adjusting means, disposed on the optical axis between the light source and the deflecting member, for displacing the position of the focal point in the radial direction.

According to this embodiment, after the light generated at the light source is two-dimensionally scanned by the optical scanning unit, the light is incident on the body lumen via the objective lens, and the return light from the body lumen is detected by the optical detector via the objective lens and the optical scanning unit. Since the small-diameter end section is provided on the objective lens and the deflecting member is provided at the small-diameter end section, the focal point can be disposed on the inner wall surface of the body lumen outward from the small-diameter end section in the radial direction. Then, by operating the focal-position adjusting means so as to displace the position of the focal point in the radial direction, a desired examination site can be focused, and a clear image can be obtained.

In this aspect, the focal-position adjusting means may adjust the focal point by changing the focal distance of a lens. It is preferable that the above-described aspect provide a pinhole at an imaging position conjugate with the focal point disposed upstream of the optical detector.

In this way, a clear image can be acquired by limiting the depth of field by the pinhole and detecting only the return light returning from an area in a shallow depth close to the focal point. By adjusting the diameter of the pinhole, the depth of field can be adjusted.

The fifth aspect of the present invention provides a microscope examination method including an insertion step of inserting a small-diameter end section of an objective lens, whose focal point is disposed outward in the radial direction, into a body lumen of a laboratory animal prepared so that a specific site generates light; a focal-position adjustment step of focusing at the light-generating site on the inner wall of the body lumen; and an image-acquisition step of acquiring an image of the in-focused light-generating site, wherein the focal-position adjustment step and the image-acquisition step are repeated while moving the small-diameter end section inside the body lumen.

According to this aspect, a two-dimensional image of a predetermined region of the inner wall of the body lumen can be acquired by repeating the step of acquiring an image by focusing at the light-generating site of the inner wall of the body lumen and the step of moving the small-diameter end section while maintaining the small-diameter end section of the objective lens with a focal point disposed outward in the radial direction.

In this aspect, a step of moving the focal position in the radial direction of the small-diameter end section may be carried out between the focal-position adjustment step and the image-acquisition step.

In this way, a three-dimensional image of a predetermined region of the inner wall of the body lumen can be acquired.

The third to fifth aspects are advantageous in that an examination site positioned on the surface of the wall of the body lumen of a laboratory animal can be clearly and constantly examined.

DETAILED DESCRIPTION OF THE INVENTION

First Embodiment

An in-vivo examination apparatus 1 and an in-vivo examination method according to a first embodiment of the present invention will be described below with reference to FIGS. 1 to 3.

Figure 1:
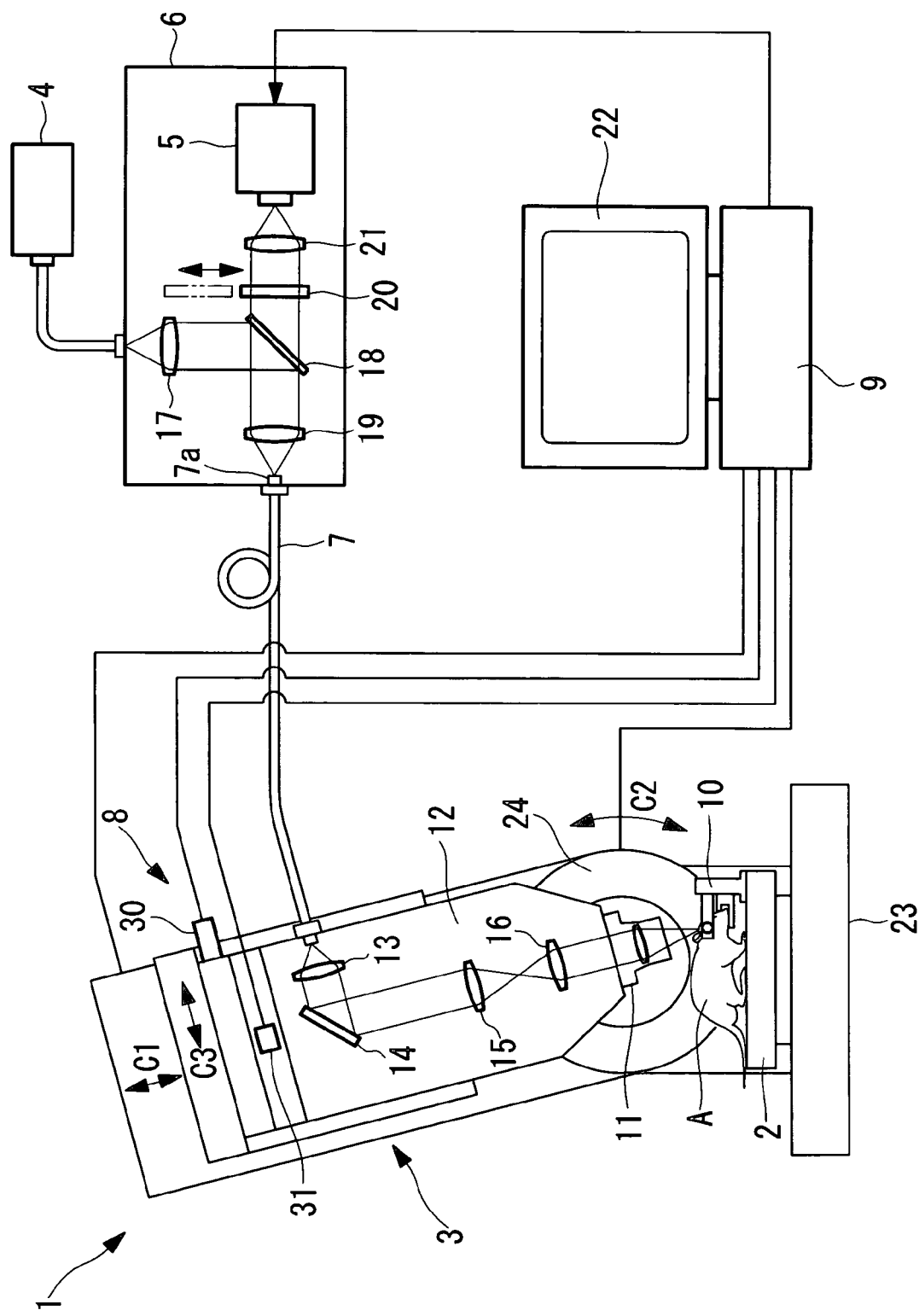
FIG. 1 is a front view illustrating the overall structure of an in-vivo examination apparatus according to a first embodiment of the present invention.
Figure 2:
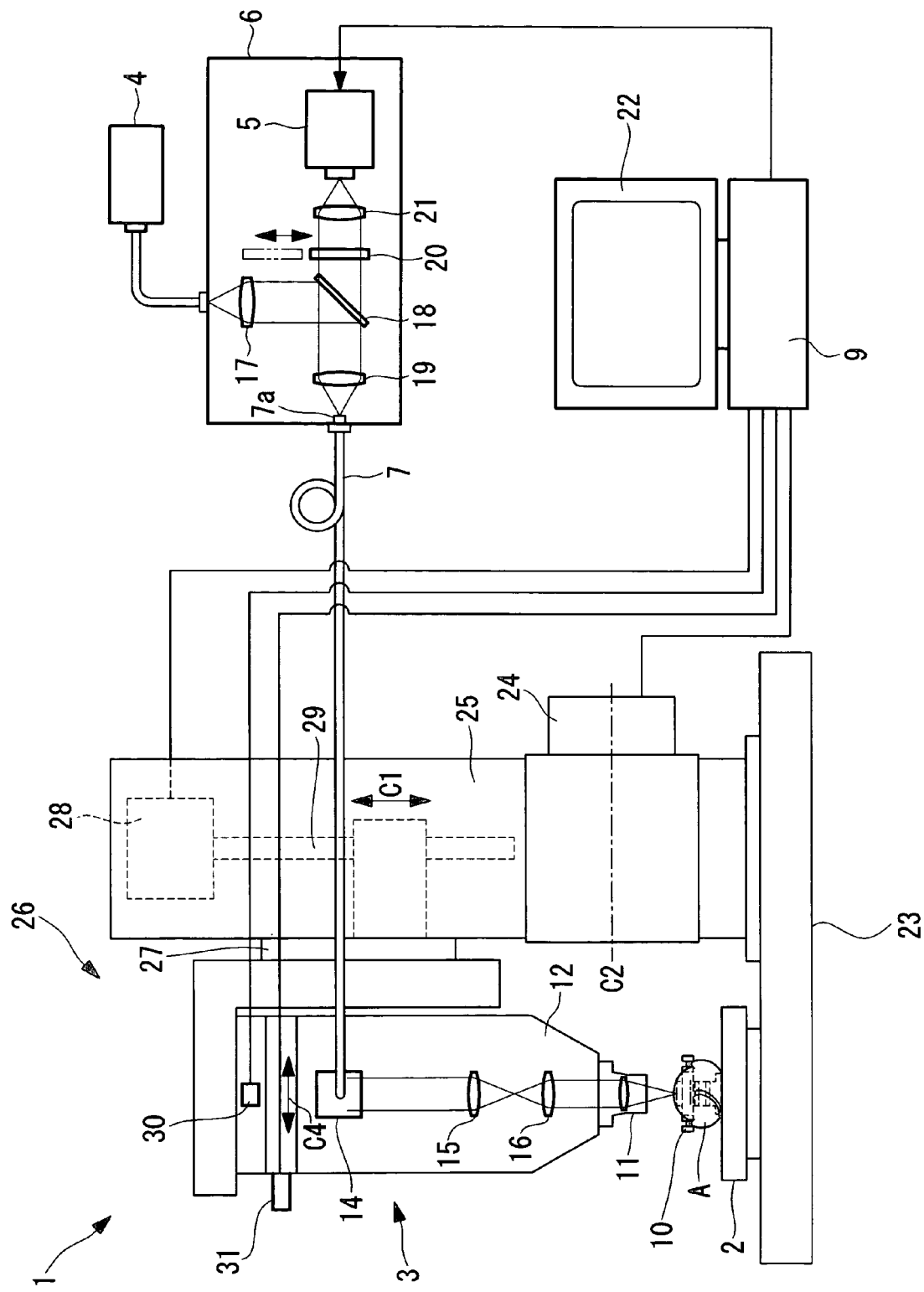
FIG. 2 is a side view illustrating the overall structure of the in-vivo examination apparatus shown in FIG. 1.

As shown in FIG. 1, the in-vivo examination apparatus 1 according to this embodiment is a laser-scanning microscope and includes a stage 2 on which an organism A to be examined is placed, a measurement head 3 that is positioned opposite to the stage 2, an optical unit 6 having a laser light source 4 and an optical detector 5, an optical fiber 7 that connects the measurement head 3 and the optical unit 6, an orientation changing mechanism 8 that supports the measurement head 3 such that the orientation of the measurement head 3 can be changed, and a control device 9 that controls the operation of the orientation changing mechanism 8.

The stage 2 is an examination platform on which the organism A to be examined is placed and includes a head-fixing unit 10 that holds the head of the organism A so as to immobilize the examination site when examining the brain.

The measurement head 3 includes an objective optical system 11 that is disposed at the tip of the measurement head 3 in such a manner as to oppose the stage 2, a collimating optical system 13 that is disposed inside a chassis 12 on which the objective optical system 11 is attached, an optical scanning unit 14, a pupil-projection optical system 15, and an imaging optical system 16.

The objective optical system 11 is, for example, a small-diameter objective lens allowing examination of the inside of the organism A, such as a small laboratory animal, e.g., a mouse. The collimating optical system 13 converts laser light that is transmitted through the optical fiber 7 into substantially collimated light. The optical scanning unit 14, which is schematically illustrated in the drawing, is capable of two-dimensionally scanning the collimated light from the collimating optical system 13 by pivoting two galvanometer mirrors around two mutually orthogonal axes.

The pupil-projection optical system 15 focuses the laser light scanned by the optical scanning unit 14 so as to form an intermediate image. The imaging optical system 16 collects the laser light forming the intermediate light and converts the focused laser light into substantially collimated light.

The objective optical system 11 is disposed close to the organism A placed on the stage 2. The objective optical system 11 focuses the substantially collimated light from the imaging optical system 16 at a focal position on the surface of the organism A or the inner tissue of the organism A.

The optical unit 6 includes a collimating lens 17 that converts the laser light generated at the laser light source 4 into substantially collimated light, a dichroic mirror 18 that reflects the laser light and transmits the return light returning to the optical unit 6, a focusing lens 19 that focuses the laser light reflected at the dichroic mirror 18 onto an end surface 7a of the optical fiber 7, a barrier filter 20 that can be move into and out of the optical path and that selectively transmits the return light in a specific wavelength band that is transmitted through the dichroic mirror 18 and blocks the light in other wavelength bands, and a focusing lens 21 that focuses the return light transmitted through the dichroic mirror 18 at the optical detector 5.

The optical detector 5 is, for example, a photomultiplier. The optical detector 5 is connected to a monitor 22 via an image-processing device (not shown) in the control device 9, and captured images are displayed on the monitor 22.

The barrier filter 20 transmits only light in a specific wavelength band. Only fluorescence that is transmitted through the barrier filter 20 is incident on the optical detector 5.

The optical fiber 7 is connected to the optical unit 6 and the measurement head 3. The optical fiber 7 transmits the laser light from the optical unit 6 into the measurement head 3 and transmits the return light from the measurement head 3 into the optical unit 6.

The orientation changing mechanism 8 includes a base 23, an arm 25 that is rotatable around a horizontal axis C2 (θ axis) by a motor 24 fixed to the base 23, and a driving mechanism 26 that is capable of driving the measurement head 3, which is attached to the arm 25, in three axial directions, i.e. a direction C1 along the optical axis (Z axis) and directions C3 and C4 (along the X and Y axes, respectively) orthogonal to the direction C1. The arm 25 may be manually rotated with a handle or the like, without using the motor 24.

A Z-axis driving mechanism of the driving mechanism 26 includes, for example, a slider 27 that is supported so as to be movable in the Z-axis direction along a liner guide (not shown), a motor 28 that drives the slider 27 in the Z-axis direction, and a ball screw 29. The slider 27 is fixed to the measurement head 3. Therefore, by operating the motor 28 so as to rotate the ball screw 29, the measurement head 3, which is fixed to the slider 27, can be moved in the direction C1 along the optical axis.

X- and Y-axis driving mechanisms include motors 30 and 31, respectively, ball screws (not shown), and sliders (not shown). By operating the motor 30, the ball screw (not shown) is rotated, allowing the measurement head 3, which is fixed to the slider (not shown), to move in the X-axis direction, whereas by operating the motor 31, the ball screw (not shown) is rotated, allowing the measurement head 3, which is fixed to the slider (not shown), to move in the Y-axis direction.

The control device 9 is connected to the motors 24, 28, 30, and 31 of the orientation changing mechanism 8 and is capable of controlling the orientation of the measurement head 3.

The control device 9 includes insertion instructing means for instructing the insertion and retraction of the barrier filter 20 for switching between reflected-light examination and fluoroscopy and reference-location setting means for storing the Z-axis position address and setting this position as a reference location 0. Operation instructions can be applied to each means via a button displayed on the monitor 22 or via input means (not shown). The control device may be constituted of a device such as a general personal computer.

Next, the operation of the in-vivo examination apparatus 1 according to this embodiment, having the above-described structure, will be described.

When the optical unit 6 is operated and laser light is emitted from the laser light source 4, the emitted laser light is focused on the end surface 7a of the optical fiber 7 after passing through the collimating lens 17, the dichroic mirror 18, and the focusing lens 19 and then is guided into the measurement head 3.

The laser light that is incident on the end surface 7a of the optical fiber 7 travels along the path via the optical fiber 7, the measurement head 3, the collimating optical system 13, the optical scanning unit 14, the pupil-projection optical system 15, and the imaging optical system 16, which are all disposed inside the measurement head 3, and is finally focused at a focal position inside the organism A. Fluorescence that is generated by a reaction in the tissue when the organism A is irradiated with the laser light returns via the objective optical system 11, the imaging optical system 16, the pupil-projection optical system 15, the optical scanning unit 14, and the collimating optical system 13 and enters the optical fiber 7. Then the fluorescence is converted into substantially collimated light by the focusing lens 19 of the optical unit 6, passes through the dichroic mirror 18, and is incident on the optical detector 5 via the focusing lens 21. A detection signal from the optical detector 5 is sent to the control device 9 for image processing and is displayed as an image on the monitor 22.

The driving mechanism 26 is capable of driving the measurement head 3 in three axial (X-, Y-, and Z-axis) directions, and the control device 9 is capable of controlling the driving distance. Therefore, the measurement head 3 can be driven three-dimensionally to the examination site in the brain. Since the orientation changing mechanism 8 is constituted of the arm 25 and the driving mechanism 26, which is movable in three axial directions, the angle of the θ axis of the measurement head 3 can be adjusted freely in a plane parallel to the rotational plane of the arm 25 while keeping the focal position of the objective optical system 11 fixed. Therefore, insertion into the cranial bone and examination of brain cells can be carried out by approaching the site to be examined at the correct angle.

Next, an in-vivo examination method using the in-vivo examination apparatus 1 according to this embodiment, having the above-described structure, will be described with reference to the flow chart in FIG. 3.

For example, to examine the brain of an organism A, such as a small laboratory animal, e.g., a mouse, the head of the organism A is immobilized with the head-fixing unit 10 so that the site to be examined is not displaced due to movement of the organism A. Then, the skin on the head is incised to expose the cranial bone, and a hole is formed in the cranial bone at the site to be examined using a drill or the like.

At this point, the barrier filter 20 is moved out of the optical path so as to switch from fluoroscopy to reflected-light examination, such as bright-field examination (S1).

Subsequently, the angle of the θ axis of the measurement head 3 is adjusted by rotating the arm 25, and the objective optical system 11 is inserted. Then, while moving the measurement head 3 in the Z-axis direction, a reflected-light examination image is confirmed.

When the objective optical system 11 reaches a position on the surface of the brain tissue, the position addresses of the X-, Y-, Z-, and θ-axis directions are stored. These position addresses define a reference position 0 (S4).

The barrier filter 20 is then moved into the optical path by driving a switching device (not shown).

In this way, the examination mode changes from reflected-light examination to fluoroscopy, allowing fluoroscopy to be carried out (S5).

Subsequently, the measurement head 3 is automatically moved by the control device 9 in the Z-axis direction to a site in the brain tissue to be examined. Once the objective optical system 11 is inserted into to the brain tissue, the shape of the brain tissue changes. Therefore, the movement may be set so that the objective optical system 11 is stopped short of the site to be examined and does not pass by the site to be examined.

For example, when the site to be examined is at a depth of 5.0 mm from the brain surface, by inputting the distance (5.0 mm) using an input device (not shown) of the control device 9, automatic detection driving by the control device 9 is carried out from the reference position 0 to a depth of 4.0 mm, which is short of the examination site (S6 and S7). At this time, the driving speed of the driving mechanism 26 is a speed that allows the objective optical system 11 to reliably stop at a depth of 4.0 mm. The position where the objective optical system 11 is temporarily stopped short of the examination site and where the driving speed is changed is instructed in advance using the input means (not shown) of the control device 9.

From the depth of 4.0 mm, the objective optical system 11 is slowly driven while the object to be examined is viewed in a fluorescence image (S8). When the examination site is found, the driving is stopped, and detailed examination is carried out (S9).

In this embodiment, the driving mechanism 26 is automatically controlled by the control device 9 when the measurement head 3 is moved to the site to be examined (S8). Instead of this, however, manual driving may be carried out. Furthermore, the driving mode may be freely switched between manual and automatic driving by using the input means of the control device 9.

In this embodiment, when calculating the driving distance (S7), a margin is included in the calculation. However, when the distance to the site to be examined is accurately known, the driving can be carried out without including a margin. The margin may be freely set by using the input means of the control device 9.

Second Embodiment

Figure 4:
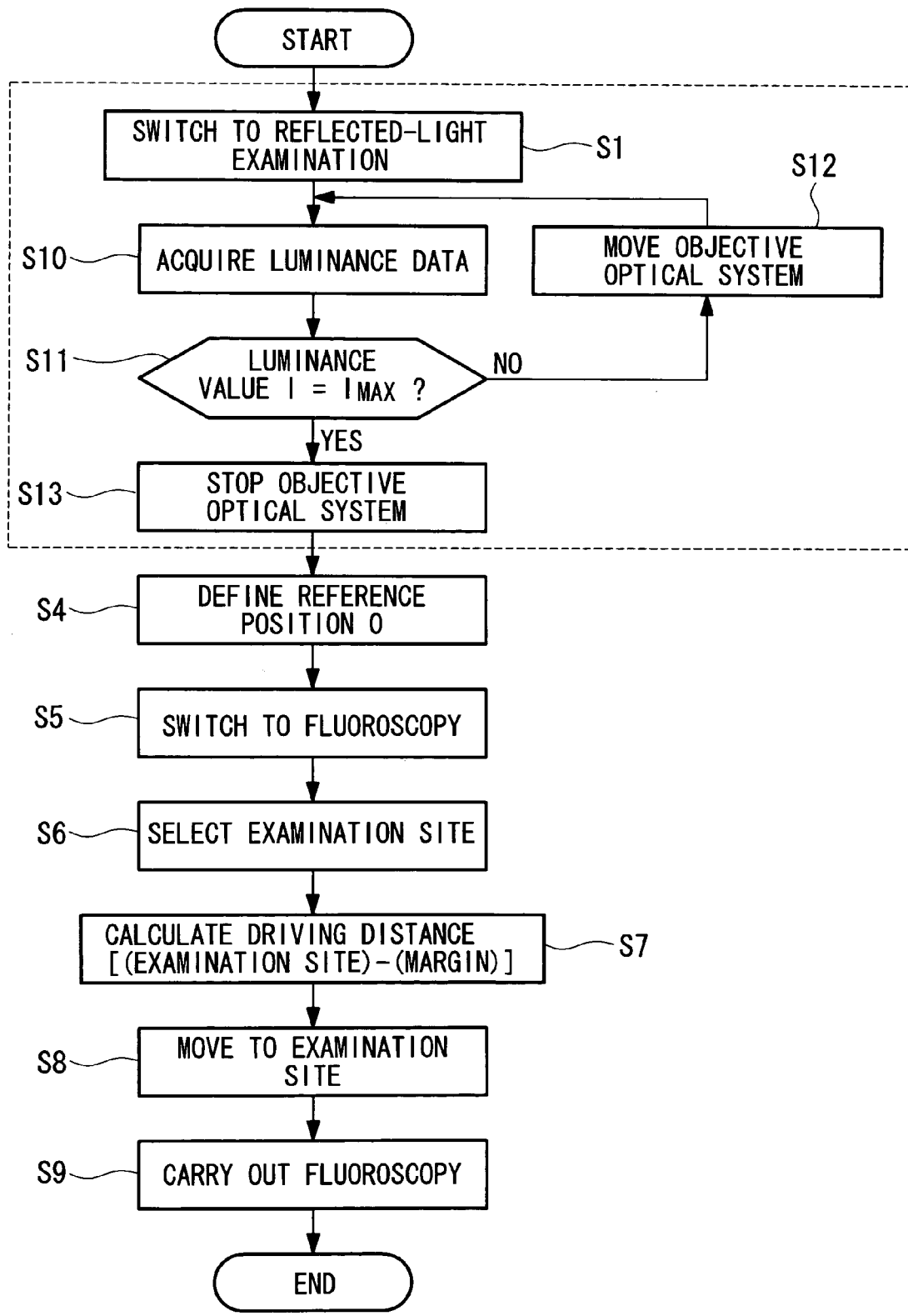
FIG. 4 is flow chart illustrating an in-vivo examination method according to a second embodiment of the present invention.

Next, an examination method according to a second embodiment will be described with reference to FIG. 4.

This embodiment is the same as the above-described in-vivo examination apparatus 1 according to the first embodiment, except that means for automatically detecting a surface location on the brain tissue is added. Since the general structure of the examination apparatus is the same as that illustrated in FIGS. 1 and 2, the examination apparatus will be described with reference to these drawings.

The in-vivo examination apparatus 1 according to the second embodiment has the same structure as that according to the first embodiment, except that the control device 9 includes an auto-focus (AF) mechanism.

The examination method according to this embodiment will be described with reference to the flow chart in FIG. 4. The method of examining by switching to fluoroscopy (S5 to S9) after setting the reference position (S4) is the same as that shown in FIG. 3. A method of detecting a surface location on the brain tissue by using reflected-light examination, shown in FIG. 3 (S2 and S3), will be described with reference to FIG. 4.

A surface location on the brain tissue is detected by, for example, the automatic focal position detection method disclosed in Japanese Unexamined Patent Application, Publication No. 2001-59935. That patent document discloses a laser-scanning microscope having a structure that is the same as that of the microscope apparatus according to this embodiment and discloses an example of an AF mechanism for reflected-light examination by the laser-scanning microscope.

By carrying out reflected-light examination, a processor (not shown) in a control device 9 acquires a luminance value I of an examination image (S10) and determines the location where the luminance value is the maximum value $I_{MAX}$ as a focal position (S11). While detecting the change in the luminance value I, the measurement head 3 is automatically moved by the control device 9 (S12), and the focal point is detected at a point where the luminance value reaches the maximum value $I_{MAX}$ (S13). The measurement head 3 is stopped at this point.

In this embodiment, a passive AF mechanism that carries out an AF operation by detecting a change in the luminance value of the examination image is employed. However, the same advantages may be achieved by employing an active AF mechanism that carries out an AF operation by emitting an infrared laser beam to a specimen and detecting the state of the reflected light or by employing other types of AF mechanisms.

Third Embodiment

Figure 5:
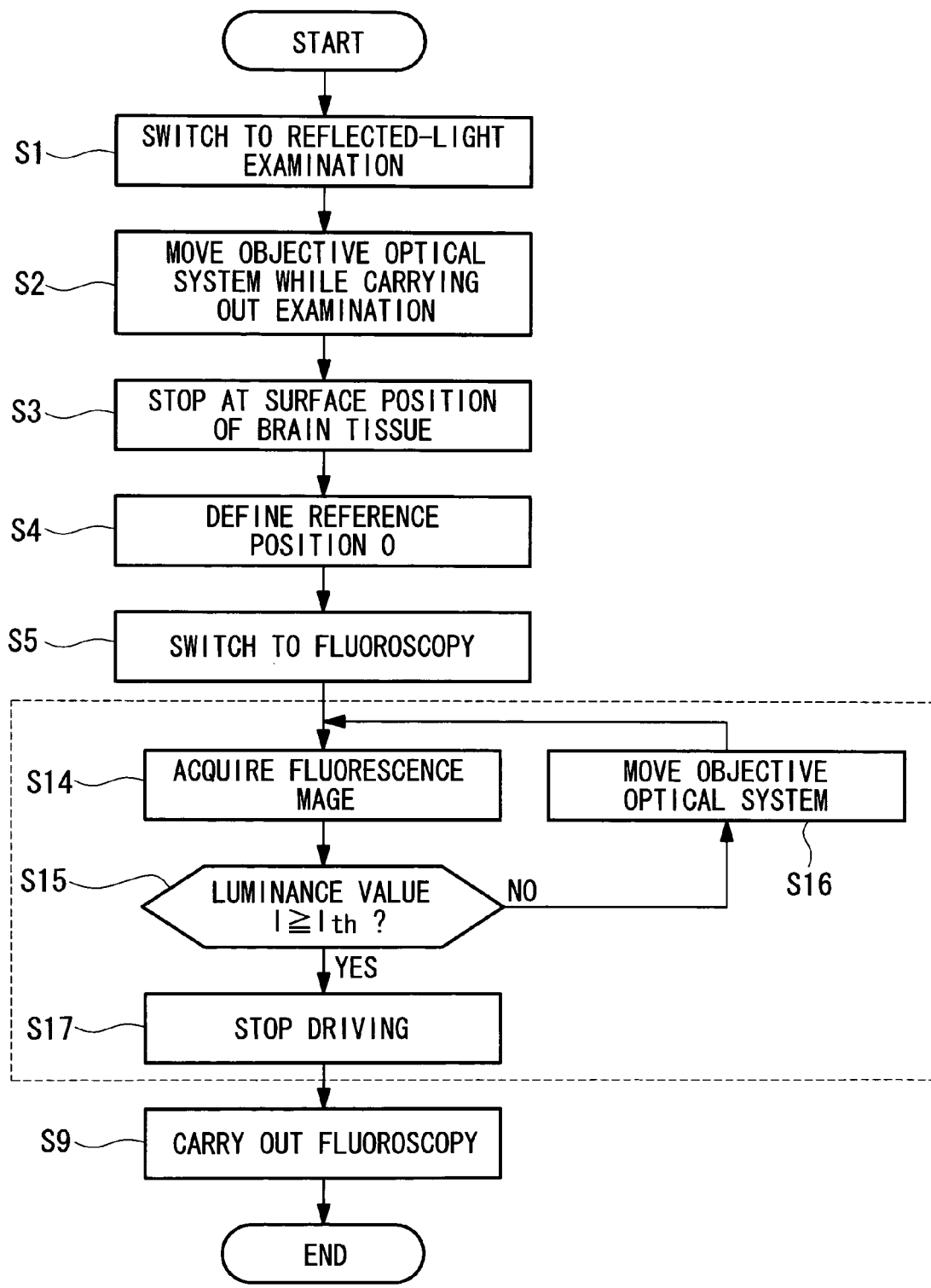
FIG. 5 is flow chart illustrating an in-vivo examination method according to a third embodiment of the present invention.

Next, an examination method according to a third embodiment will be described with reference to FIG. 5.

This embodiment is the same as the above-described in-vivo examination apparatus 1 according to the first or second embodiment, except that means for detecting an examination site in brain tissue is added. Since the general structure of the examination apparatus is the same as that illustrated in FIGS. 1 and 2, the examination apparatus will be described with reference to these drawings.

The in-vivo examination apparatus according to this embodiment differs from the in-vivo examination apparatus 1 according to the first embodiment in that a processor (not shown) in the control device 9 includes means for measuring the average luminance value of an image acquired by fluoroscopy and means for setting a threshold value of the average luminance value with an input device (not shown) in the control device 9. The remaining structures are the same as those of the in-vivo examination apparatus 1 according to the first embodiment.

The examination method according to this embodiment will be described with reference to the flow chart in FIG. 5.

Figure 3:
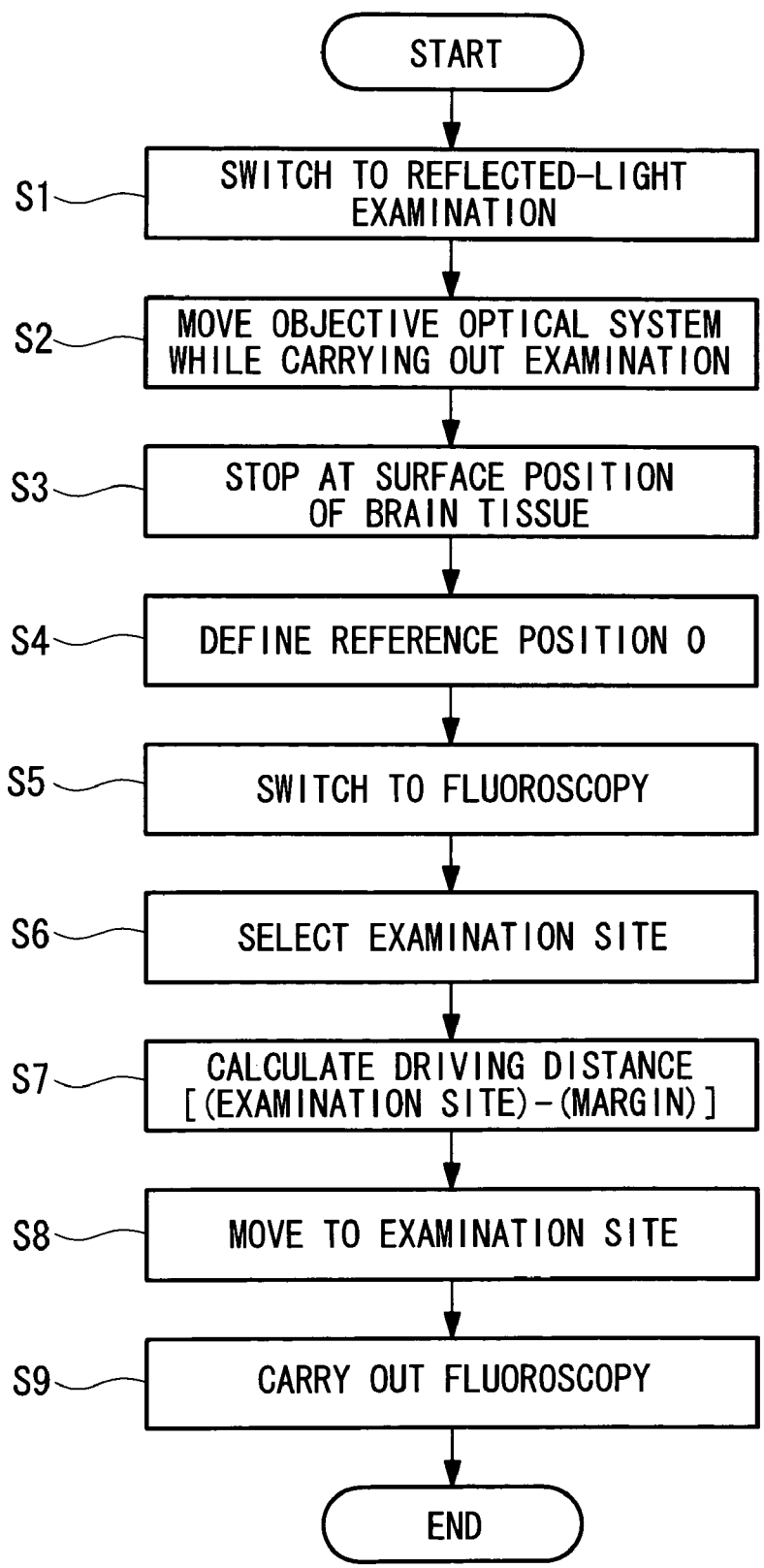
FIG. 3 is flow chart illustrating an in-vivo examination method according to an embodiment of the present invention employing the in-vivo examination apparatus shown in FIG. 1.

The process of setting a surface location on brain tissue as a reference position in reflected-light examination and then switching to fluoroscopy (S1 to S5) is the same as that according to the first embodiment shown in FIG. 3.

In the examination method according to this embodiment, an examination site is detected by carrying out the following process.

First, by acquiring a fluorescence image, the processor (not shown) in the control device 9 acquires an average luminance value I of the fluorescence image (S14). Since the luminance value is a maximum value at the focal position, the measurement head 3 is moved automatically by the control device 9 (S16) while detecting the change in the luminance value. A position where the average luminance value I equals or exceeds a preset threshold value $I_{th}$ is defined as the examination site, and the movement of the measurement head 3 is stopped (S17).

According to this embodiment, the average luminance value I of the fluorescence image is measured. However, the examination site may be detected by using other methods, such as detection based on a change in contrast of the fluorescence image.

According to this embodiment, the examination site is detected on the basis of the luminance value of the image. When the same examination as the previous examination is to be repeatedly carried out at the same site on a specimen, a fluorescence image is displayed on the monitor 22. Then, the examination site may be detected by extracting several fluorescence images that were previously examined and comparing whether or not the shape of these images is the same.

Fourth Embodiment

Figure 6:
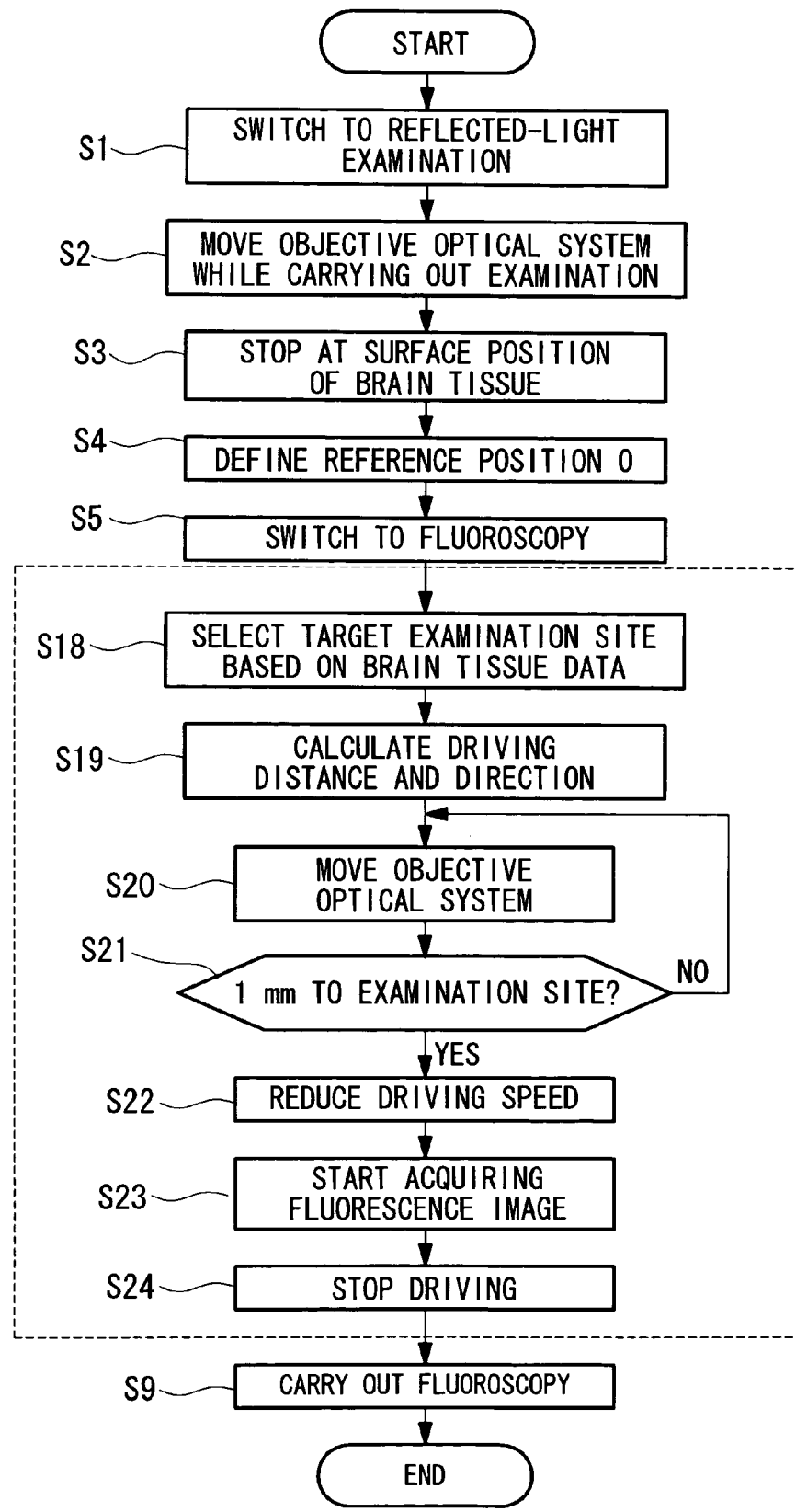
FIG. 6 is flow chart illustrating an in-vivo examination method according to a fourth embodiment of the present invention.

Next, an in-vivo examination apparatus and an examination method according to a fourth embodiment will be described with reference to FIG. 6.

The in-vivo examination apparatus according to this embodiment is the same as the in-vivo examination apparatus 1 according to the first embodiment, except that means for detecting an examination site using in-vivo information is added. Since the general structure of the examination apparatus is the same as that illustrated in FIGS. 1 and 2, the examination apparatus will be described with reference to these drawings.

The examination method according to this embodiment is the same as the examination method according to the first embodiment, except that data of brain tissue is used to carry out driving to the examination site after a surface location on the brain tissue is detected.

The control device 9 stores in-vivo information, such as data on brain tissue of a small laboratory animal, e.g., a mouse, and drives the orientation changing mechanism 8 to the examination site on the basis of the in-vivo information. The in-vivo information is, for example, data such as an atlas that defines a three-dimensional map in the control device 9 and that can be displayed on the monitor 22.

The process of defining the surface location on the brain tissue as a reference position in reflected-light examination and then switching to fluoroscopy (S1 to S5) is the same as that according to the first embodiment shown in FIG. 3.

In the examination method according to this embodiment, first a reference position is defined and then the examination mode is switched to fluoroscopy, in the same manner as in the examination method according to the first embodiment shown in FIG. 3 (S1 to S5). Subsequently, as shown in FIG. 6, a current examination site that is currently being examined using the measurement head 3 and a target examination site in the brain tissue that is to be examined next are assigned (S18) on the three-dimensional data map of brain tissue of a small laboratory animal, such as a mouse, that is stored in the control device 9 and displayed on the monitor 22. In the control device 9, the driving distance and directions of the X-, Y-, and Z-axes from the reference position to the target examination site are calculated on the basis of the current examination site and the target examination site that are assigned and the reference position defined in Step S4 (S19).

The insertion angle of the objective optical system 11 is determined at the control device 9 on the basis of the calculated distance and angle to the target examination site. Then, the arm 25 is driven to operate the driving mechanism 26 so as to automatically move the measurement head 3 to the target examination site in the brain tissue (S20). When the measurement head 3 moves to a point close to, for example, 1 mm away from the target examination site that is assigned in advance using an input means (not shown) of the control device 9, the driving speed of the measurement head 3 is reduced (S21 and S22). Then, while observing the examination site on the fluorescence image (S23), the measurement head 3 is automatically moved by the control device 9. When the measurement head 3 reaches the target examination site, driving is stopped, and detailed examination is carried out (S24 and S9).

In this embodiment, the driving speed is reduced from a point close to the target examination site. However, the driving speed does not have to be changed until the target examination site is reached so long as the measurement head 3 is reliably stopped and the target examination site is accurately determined.

In this embodiment, the measurement head 3 is automatically moved from a point close to the target examination site to the actual target examination site. However, the target examination site may be searched for by manually driving the measurement head 3. Furthermore, it is possible to freely switch between manual driving and automatic driving using the input means of the control device 9.

In this embodiment, an atlas stored in the control device 9 is used as brain data. However, brain tissue data of an individual organism A may be acquired in advance using an apparatus such as a CT or an MRI, which is used for in-vivo examination. By using brain data of an individual organism, more accurate data can be employed.

The size of the skull and the positions of the sutures at the upper part of the skull are substantially identical for laboratory animals that are the same age in weeks. Thus, the position of a suture may define a reference for finding an examination site and then driving the orientation changing mechanism 8 to the examination site.

In this embodiment, the objective optical system 11 is fixed to the chassis 12 of the measurement head 3 so that the objective optical system 11 is driven together with the measurement head 3 by the driving mechanism 26. Instead of this, however, the chassis 12 of the measurement head 3 may be fixed to the base 23, and another driving mechanism for driving the objective optical system 11 with respect to the chassis 12 may be provided. Instead of driving the objective optical system 11, a driving mechanism for driving the stage 2 may be provided.

In this embodiment, a method of examining brain tissue of a living organism is described. However, the embodiment is not limited thereto, and the method may be employed for examining tissue of other parts of the body of the living organism.

In this embodiment, a case in which a laser-scanning microscope is employed is described. However, the embodiment is not limited thereto, and other types of microscope apparatuses and examination apparatuses may be employed.

Fifth Embodiment

An objective lens and a microscope apparatus according to a fifth embodiment of the present invention will be described below with reference to FIGS. 7 and 8.

Figure 7:
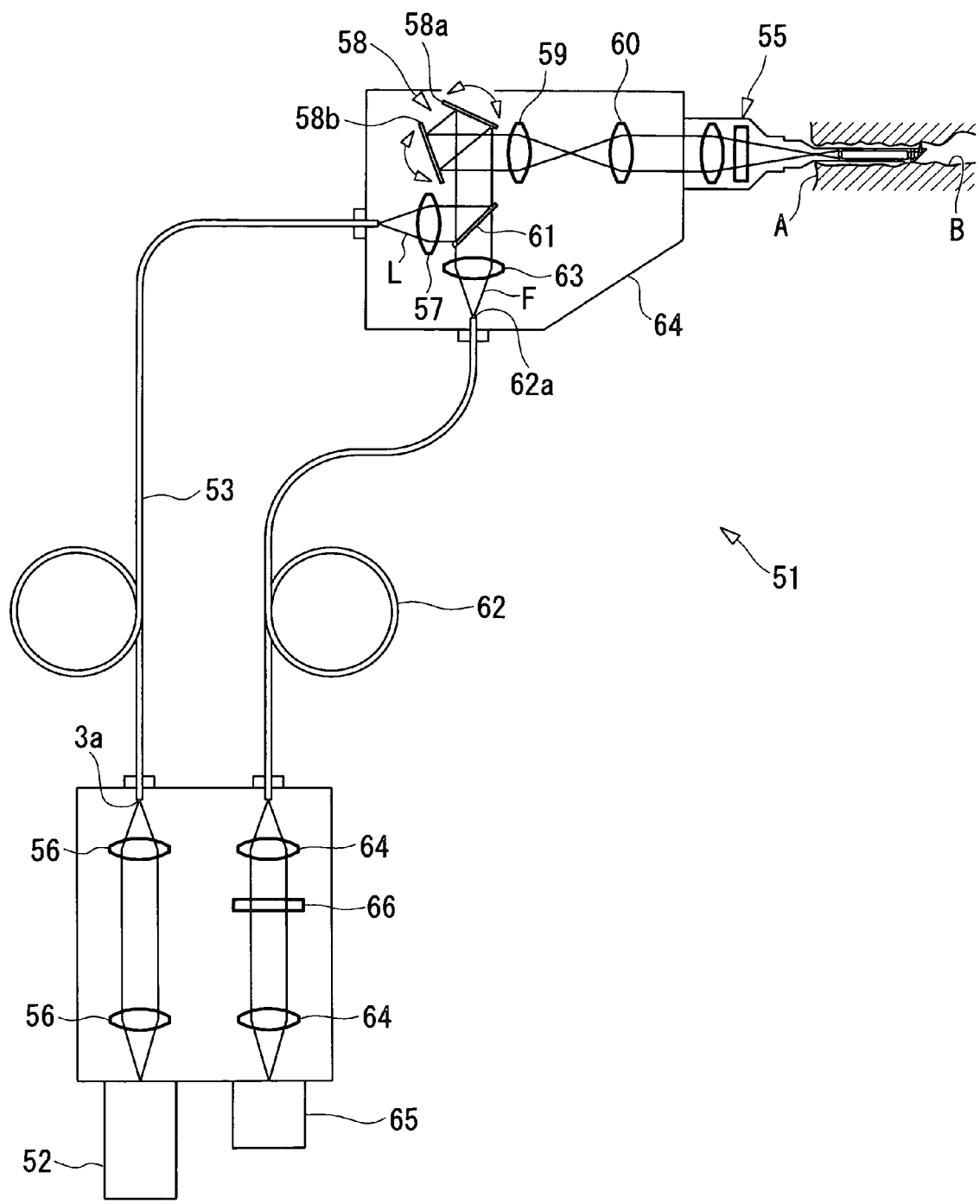
FIG. 7 is a schematic view of the overall structure of a microscope apparatus according to a fifth embodiment of the present invention.

As shown in FIG. 7, a microscope apparatus 51 according to this embodiment includes a light source 52 that generates laser light L, an optical fiber 53 that transmits the laser light L generated at the light source 52, a microscope main body 54 that is connected to the optical fiber 53, and an objective lens 55 that is attached to the microscope main body 54. The drawing also shows focusing lenses 56 that focus the laser light L onto the end surface 53a of the optical fiber 53.

The microscope main body 54 includes a collimating lens 57 configured to convert the laser light L transmitted through the optical fiber 53 into substantially collimated light, an optical scanning unit 58 configured to two-dimensionally scan the substantially collimated laser light L, a pupil-projection lens 59 configured to focus the laser light L that was two-dimensionally scanned by the optical scanning unit 58 and to form an intermediate image, and an imaging lens 60 configured to collect the laser light L forming the intermediate image to convert the collected laser light L into substantially collimated light. The optical scanning unit 58 includes, for example, proximity galvanometer mirrors including two galvanometer mirrors 58a and 58b that can pivot around two mutually orthogonal axes.

The microscope main body 54 includes a dichroic mirror 61 configured to separate from the optical path of the laser light L fluorescence F that has returned via a path including the imaging lens 60, the pupil-projection lens 59, and the optical scanning unit 58 and a coupling lens 63 configured to focus the fluorescence F separated by the dichroic mirror 61 at the end 62a of an optical fiber 62. The microscope apparatus 51 according to this embodiment includes the optical fiber 62 configured to transmit the fluorescence F focused by the coupling lens 63, a focusing lens 64 configured to collect the fluorescence F transmitted through the optical fiber 62, and an optical detector 65 configured to detect the fluorescence F focused by another focusing lens 64. The drawing also illustrates a barrier filter 66 configured to block the laser light L, which has transmitted through the optical fiber 62 together with the fluorescence F, from entering the optical detector 65. The optical detector 65 includes, for example, a photomultiplier tube (PMT).

Figure 8:
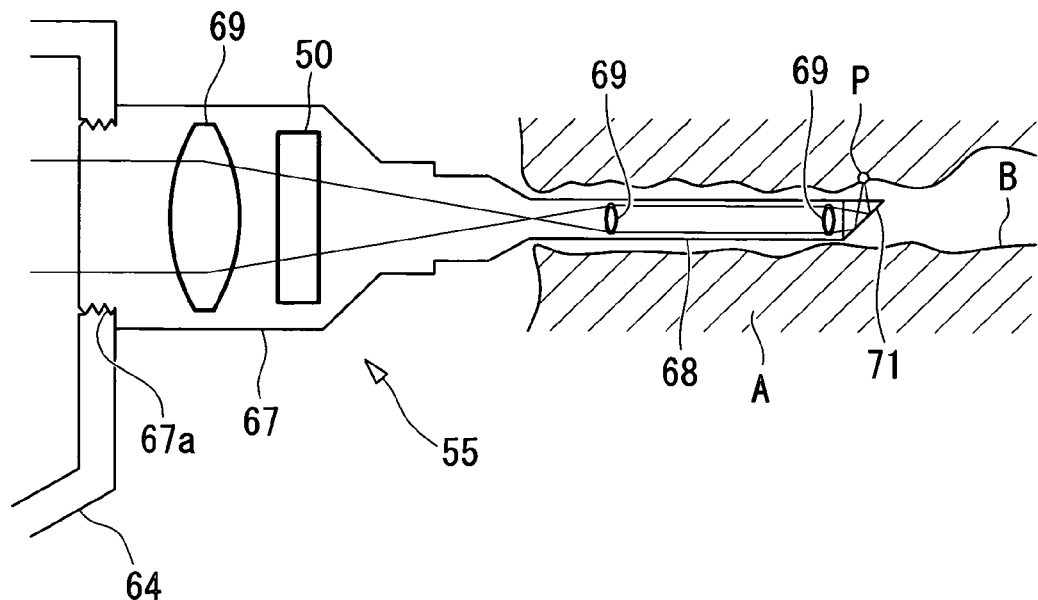
FIG. 8 is an enlarged schematic view of an objective lens of the microscope apparatus illustrated in FIG. 7.

As shown in FIG. 8, the objective lens 55 includes a small-diameter end section 68. The small-diameter end section 68 has a diameter sufficiently small that it can be inserted into a body lumen B of small laboratory animal A, such as a mouse, and is provided on a chassis 67 that includes threaded mount 67a for mounting to the microscope main body 54. The chassis 67 accommodates a plurality of relay lenses 69 for relaying the laser light L that has been converted into substantially collimated light by the imaging lens 60 and a liquid lens (focal-position adjusting means) 70. At the tip of the small-diameter end section 68, a mirror (deflecting member) 71 configured to deflect the laser light L outward in the radial direction is provided.

By changing the radius of curvature of the interface of the liquid in the liquid lens 70 by changing the applied voltage, the focal position P of the entire objective lens 55 can be moved in the optical axis direction.

The operations of the objective lens 55 and the microscope apparatus 51 according to this embodiment and having the above-described structures will be described below.

To examine the inner wall surface of the body lumen B of the small laboratory animal A using the objective lens 55 and the microscope apparatus 51 according to this embodiment, the small-diameter end section 68 provided at the tip of the objective lens 55 is inserted into the body lumen B of the small laboratory animal A, which is prepared in advance so that a specific region thereof emits light. A mouse that is genetically engineered to be prone to cancer or a mouse injected with fluorescent material that generates fluorescence F specifically in the vicinity of cancer may be used as the small laboratory animal A.

The laser light L generated at the light source 52 is transmitted through the optical fiber 53 and enters the microscope main body 54. After the laser light L is converted into substantially collimated light by the collimating lens 57, it is two-dimensionally scanned by the optical scanning unit 58. Then, the scanned laser light L enters the objective lens 55 via the pupil-projection lens 59 and the imaging lens 60, is relayed through the relay lenses 69 and the liquid lens 70 inside the objective lens 55, and is emitted from the tip of the small-diameter end section 68.

Since the mirror 71 is disposed at the tip of the small-diameter end section 68, the laser light L that is transmitted through the small-diameter end section 68 in the longitudinal axis direction is deflected outward in the radial direction and is focused at a focal position P that is positioned outward of the small-diameter end section 68 in the radial direction. Since the inner wall surface of the body lumen B of the small laboratory animal A is disposed close to and outward from the small-diameter end section 68 in the radial direction, the laser light L is easily focused at the of the inner wall surface, causing the fluorescent material in the body of the small laboratory animal A to be excited and generate fluorescence F.

The fluorescence F generated at the surface of the inner wall is collected by the objective lens 55 via the mirror 71, is returned via the pupil-projection lens 59 and the optical scanning unit 58, passes through the dichroic mirror 61, is collected by the coupling lens 63, and is detected by the optical detector 65 via the optical fiber 62 and the focusing lens 64. In this way, a two-dimensional fluorescence image is acquired.

With the objective lens 55 and the microscope apparatus 51, an image can be easily acquired by positioning the focal point on the inner wall surface of the body lumen B in which the small-diameter end section 68 is inserted because the mirror 71 is disposed at the tip of the small-diameter end section 68. In other words, since only the cavity of the body lumen B is disposed in front in the longitudinal direction of the small-diameter end section 68 that is inserted into the body lumen B, with conventional technologies, it is difficult to acquire an efficient fluorescence image. However, according to this embodiment, the inner wall surface can be focused so as to acquire a clear image merely by inserting the small-diameter end section 68 into the body lumen B.

According to this embodiment, the end section 62a of the optical fiber 62 functions as a pinhole that is conjugate with respect to the focal position P in front of the small-diameter end section 68 of the objective lens 55. Therefore, the depth of field is limited and a clear confocal image can be acquired. Since the liquid lens 70 is disposed inside the objective lens 55, the focal position P can be adjusted in the radial direction of the small-diameter end section 68 by adjusting the voltage applied to the liquid lens 70 so as to move the small-diameter end section 68. As a result, the examination site that is positioned in the depth direction of the inner wall of the body lumen B can be clearly and stably examined.

In particular, by employing the liquid lens 70 disposed inside the objective lens 55, the size of the objective lens 55 can be prevented from being increased, and focusing can be easily carried out.

To acquire an image of the inside of the body lumen B using the microscope apparatus 51 according to this embodiment, the small-diameter end section 68 is inserted deep inside the examination region of the body lumen B of the small laboratory animal A (Step S1), and the microscope apparatus 51 is operated. By operating the liquid lens 70, the light-generating region is focused (Step S2), and the collected fluorescence F is captured (Step S3). In this way, a two-dimensional fluorescence image of a predetermined area at the depth of the focal plane is acquired.

Then, by repeating the above-described steps (S2 and S3) while pulling out the objective lens 55 in the longitudinal direction relative to the body lumen B of the small laboratory animal A, a two-dimensional fluorescence image in the longitudinal direction of the body lumen B can be acquired. As a method of moving the objective lens 55 and the body lumen B in the longitudinal direction relative to each other, the small laboratory animal A may be fixed to a fixing stage (not shown) and the objective lens 55 may be moved in the longitudinal direction or the small laboratory animal A fixed to the movable state may be moved relative to a fixed objective lens 55.

By repeating the above-described steps (S2 and S3) while rotating the objective lens 55 in the circumferential direction relative to the body lumen B of the small laboratory animal A, a two-dimensional fluorescence image in the circumferential direction of the body lumen B can be acquired. As a method of rotating the objective lens 55 and the body lumen B in the circumferential direction relative to each other, the small laboratory animal A may be fixed to a fixing state (not shown) and the objective lens 55 may be rotated around the longitudinal axis or the small laboratory animal A fixed to a movable stage may be rotated around the longitudinal axis relative to the fixed objective lens 55.

By repeating the above-described steps (S2 and S3) while moving the focal plane in the depth direction away from the inner wall surface of the body lumen B by operating the liquid lens 70 at positions along the longitudinal direction and the circumferential direction of the body lumen B, a two-dimensional fluorescence image in the depth direction of the body lumen B can be acquired. By combining the acquired two-dimensional fluorescence images, a three-dimensional fluorescence image can be constructed.

Figure 9:
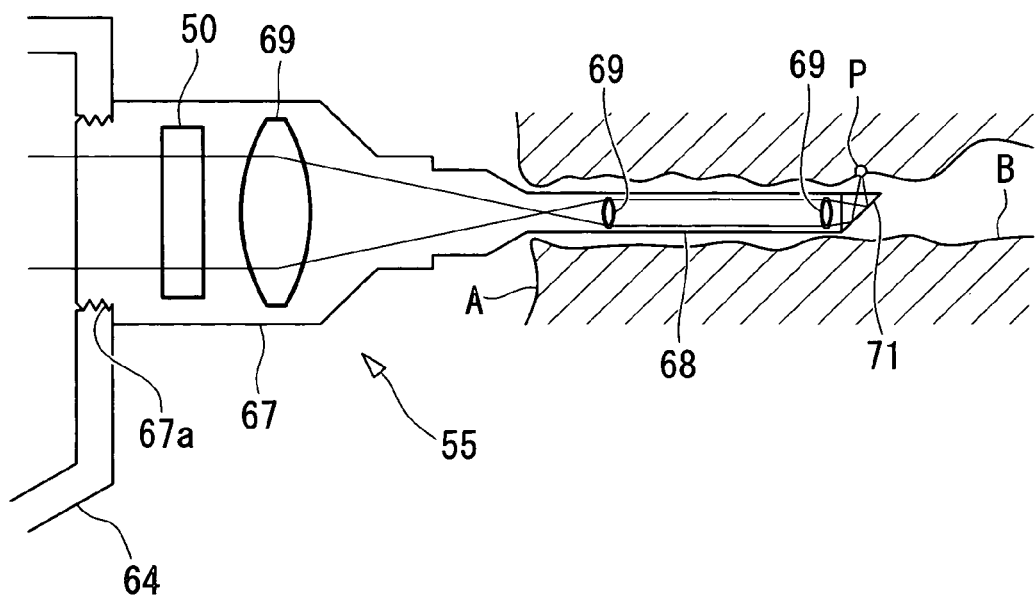
FIG. 9 is an enlarged schematic view of a modification of the objective lens illustrated in FIG. 8.

With the objective lens 55 according to this embodiment, the liquid lens 70 is disposed between the relay lenses 69. Instead of this, however, the position of the liquid lens 70 may be freely selected, as shown in FIG. 9.

With the microscope apparatus 51 according to this embodiment, the liquid lens 70 is disposed in the objective lens 55. Instead of this, however, as shown in FIGS. 10 to 12, a liquid lens may be disposed in the microscope main body 54.

Figure 10:
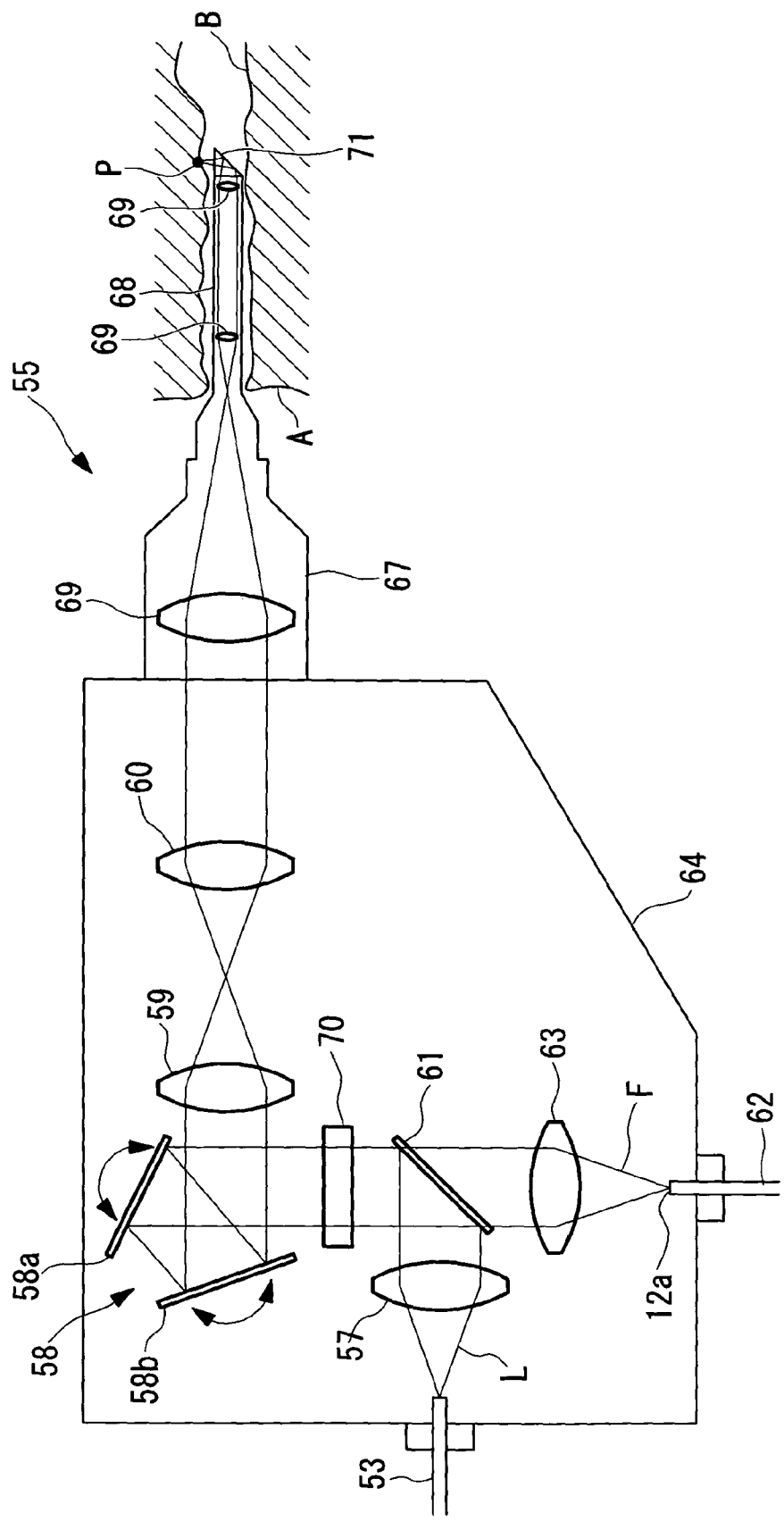
FIG. 10 is a schematic view of a first modification of the microscope apparatus illustrated in FIG. 7.

FIG. 10 illustrates a case in which the liquid lens 70 is interposed between the dichroic mirror 61 and the galvanometer mirror 58*a*. By disposing the liquid lens 70 in the path of the substantially collimated light where it is not affected by the scanning of the optical scanning unit 58, the focal position P can be moved using a relatively small liquid lens 70.

Figure 11:
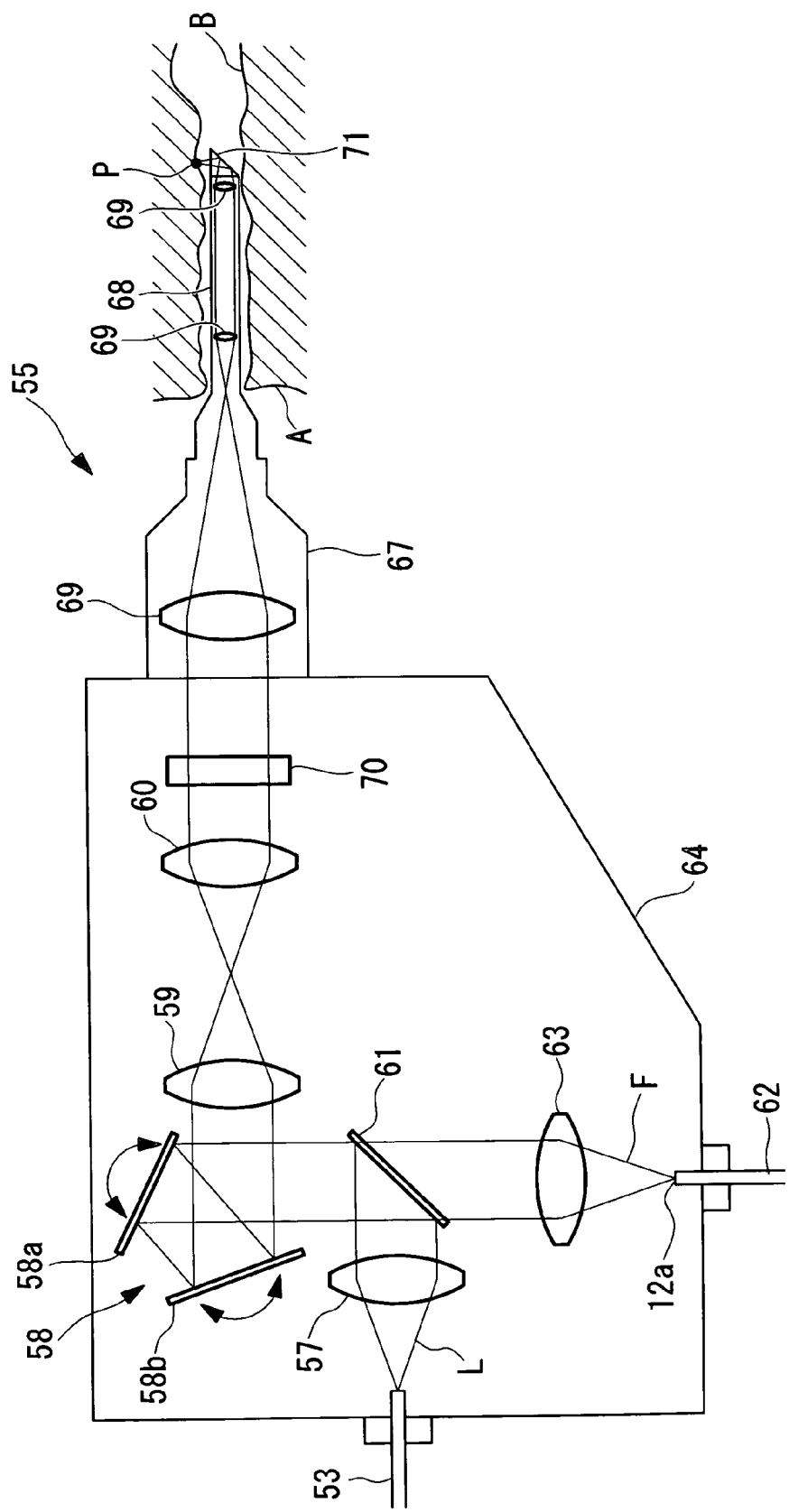
FIG. 11 is a schematic view of a second modification of the microscope apparatus illustrated in FIG. 7.
Figure 12:
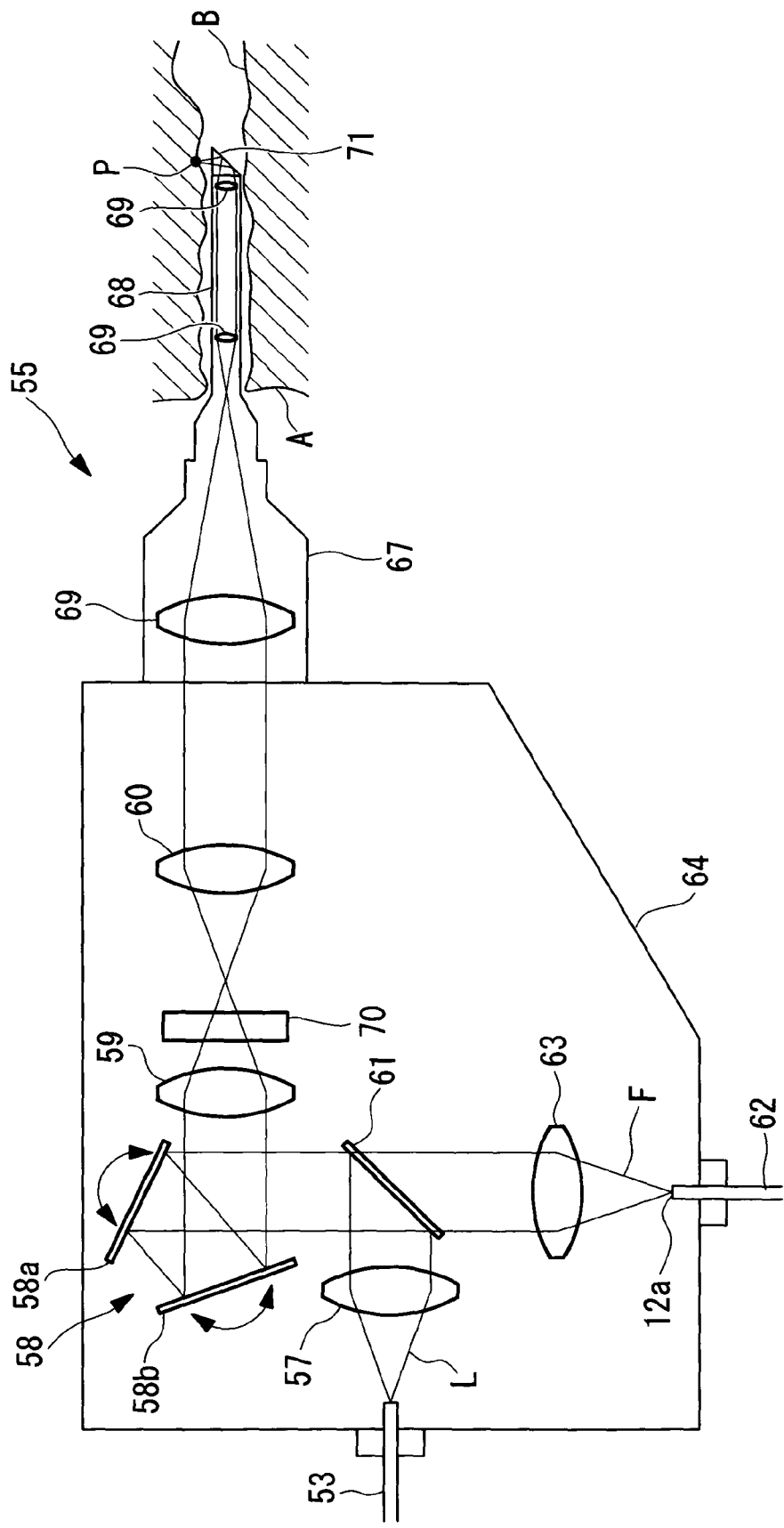
FIG. 12 is a schematic view of a third modification of the microscope apparatus illustrated in FIG. 7.

FIG. 11 illustrates a case in which the liquid lens 70 is interposed between the imaging lens 60 and the objective lens 55 in the microscope main body 54. FIG. 12 illustrates a case in which the liquid lens 70 is interposed between the pupil-projection lens 59 and the imaging lens 60.

Figure 13:
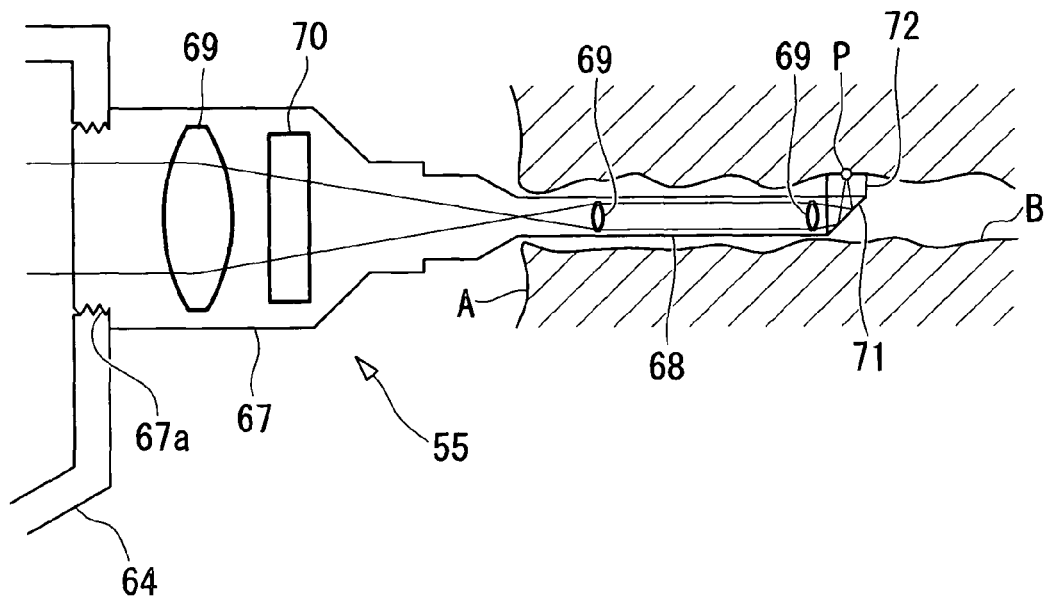
FIG. 13 is an enlarged schematic view of a modification of the objective lens illustrated in FIG. 8, wherein a transparent member is disposed at the tip of the objective lens.

With the microscope apparatus 51 and the objective lens 55 according to this embodiment, as illustrated in FIG. 13, a transparent member 72 may be provided at least in the vicinity of the focal position P, along the radial direction on the outer side of the tip of the small-diameter end section 68 of the objective lens 55. The transparent member 72 is provided in an area that is larger than the scanning range of the laser light L deflected by the mirror 71.

In this way, the inner wall surface of the body lumen B can be flattened by pressing the transparent member 72 against the surface of the inner wall, and thus, the inner wall surface can be easily focused. Furthermore, it is advantageous to press the transparent member 72 against the inner wall surface because the small-diameter end section 68 of the objective lens 55 can be fixed at a position with respect to the body lumen B and a fluorescence image with a small blur can be acquired. The transparent member 72 is only required to be disposed in an area on which the laser light L deflected by the mirror 71 is incident. However, the transparent member 72 may be provided on the entire circumference of the small-diameter end section 68.

Figure 14:
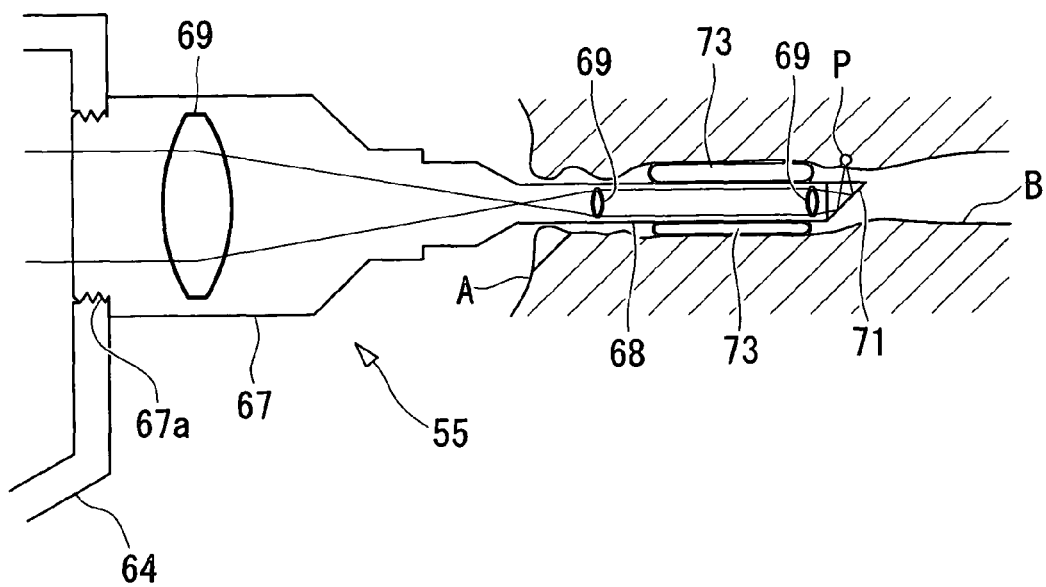
FIG. 14 is an enlarged schematic view of a modification of the objective lens illustrated in FIG. 8, wherein a balloon is disposed at the small-diameter end section of the objective lens.

Instead of the transparent member 72 that is provided for fixing the position of the small-diameter end section 68 relative to the body lumen B, as illustrated in FIG. 14, a balloon 73 may be provided around the small-diameter end section 68. In this way, by inflating the balloon 73 while the small-diameter end section 68 is inserted into the body lumen B, the position of the small-diameter end section 68 can be fixed in the radial direction with respect to the body lumen B.

As illustrated in FIG. 14, the balloon 73 that is disposed around the small-diameter end section 68 may be constructed of a plurality of balloons 73 that can be inflated or deflated independently. In this way, by inflating a balloon 73 and deflating another balloon 73, the position of the small-diameter end section 68 in the radial direction can be adjusted while fixing the position of the small-diameter end section 68 in the radial direction with respect to the body lumen B.

Therefore, by inflating or deflating the balloon 73 on the side of the focal position P and the balloon 73 on the opposite side across the small-diameter end section 68, the focal position P can be moved. As a result, focal-position adjustment means, such as the liquid lens, does not have to be provided in the microscope main body 54 or the objective lens 55, and focal position can be adjusted by the balloons 73. Any number of the balloons 73 that are individually inflatable and deflatable may be arranged along the circumferential direction. Any balloons, such as multilumen tubes, that each have a plurality of pressure chambers sectioned in the circumferential direction by a plurality of walls may be employed as the balloons 73. The fluid supplied into the balloon 73 may be liquid, such as water or oil, or gas, such as air.

Figure 15:
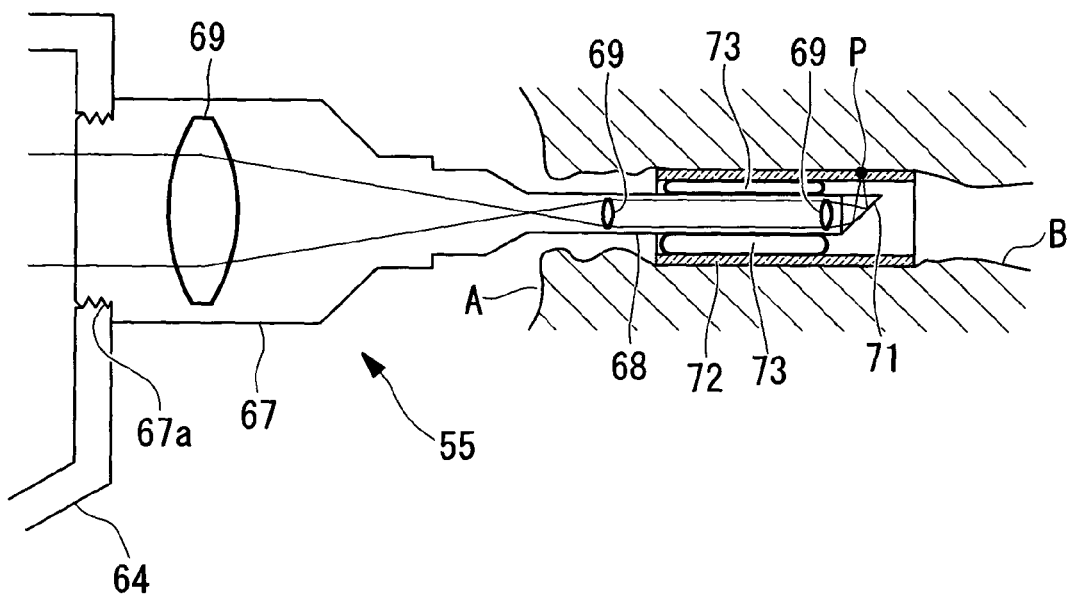
FIG. 15 is an enlarged schematic view of a modification of the objective lens illustrated in FIG. 8, wherein a balloon is interposed between a transparent member that is disposed at the tip of the objective lens and a small-diameter end section.

As illustrated in FIG. 15, a cylindrical transparent member 72 may be disposed around the small-diameter end section 68, and the balloons 73 may be interposed between the transparent member 72 and the small-diameter end section 68. In this way, examination can be easily carried out by flattening the inner wall surface of the body lumen B using the transparent member 72. In addition, by changing the level of inflation or deflation of the balloons 73 in the circumferential direction, the relative positions of the transparent member 72 and the small-diameter end section 68 can be changed in the radial direction so as to change the focal position P.

Figure 16:
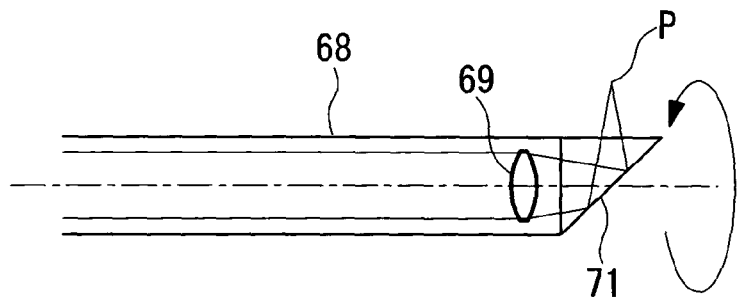
FIG. 16 is an enlarged partial view of the small-diameter end section of the objective lens illustrated in FIG. 8.

According to this embodiment, when examining a plurality of sites along the circumferential direction inside the body lumen B, as illustrated in FIG. 16, the body lumen B and the small-diameter end section 68 are rotated relative to each other around the longitudinal axis. In this case, only the mirror 71 disposed at the tip of the small-diameter end section 68 may be rotated; the small-diameter end section 68 may be rotated; or the entire objective lens 55 may be rotated. Moreover, the microscope main body 54 and the objective lens 55 may be rotated together.

Figure 17:
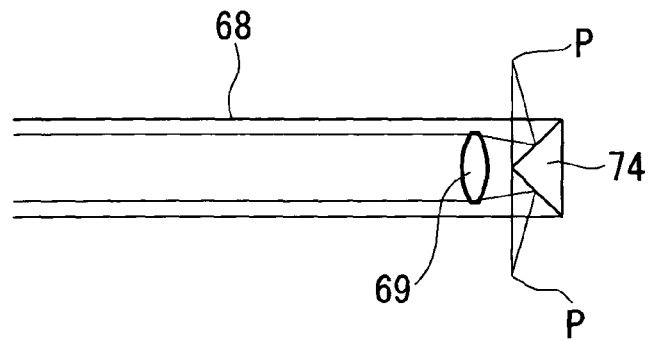
FIG. 17 is an enlarged partial view of a modification of the objective lens illustrated in FIG. 8, wherein a deflection member is provide at the small-diameter end section of the objective lens.

As shown in FIG. 17, a conic mirror 74 may be disposed as a deflecting member. In this way, a fluorescence image of the inner wall surface of the body lumen B in the entire circumferential direction can be acquired without rotating the small-diameter end section 68 and the body lumen B relative to each other.

Although the embodiments of the present invention have been described above, various modifications of the above-described embodiments may be provided within the scope of the present invention. Embodiments configured by partially combining the above-described embodiments are also included within the scope of the present invention.

Additional Items

The following configurations are derived from the embodiments described above.

Additional Item 1

An objective lens including a small-diameter end section that can be inserted into a body lumen; a deflecting member for deflecting the optical axis in a direction intersecting with the longitudinal axis so that the focal point is disposed outward of the small-diameter end section in the radial direction; and focal-position adjusting means for displacing the position of the focal point in the radial direction.

Additional Item 2

The objective lens according to Additional Item 1, wherein the focal-position adjusting means carries out focusing by changing the focal length of a lens.

Additional Item 3

The objective lens according to Additional Item 1, wherein the focal-position adjusting means includes a liquid lens.

Additional Item 4

The objective lens according to Additional Item 1, further including a transparent member that is disposed at least in the vicinity of the focal position outward of the small-diameter end section in the radial direction.

Additional Item 5

The objective lens according to Additional Item 4, wherein the focal-position adjusting means is interposed between the transparent member and the small-diameter end section and includes an actuator that changes the distance therebetween.

Additional Item 6

The objective lens according to Additional Item 1, further including fixing means, disposed in the periphery of the small-diameter end section, for fixing the small-diameter end section to the surface of the body lumen wall.

Additional Item 7

The objective lens according to Additional Item 6, wherein the fixing means includes a balloon.

Additional Item 8

The objective lens according to Additional Item 7, wherein the balloon is divided into a plurality of sections in the circumferential direction, and each section is independently inflatable or deflatable.

Additional Item 9

The objective lens according to Additional Items 1 to 8 further including a rotating mechanism that rotates the deflecting member around the longitudinal axis of the small-diameter end section.

Additional Item 10

The objective lens according to Additional Items 1 to 8, wherein the deflecting member includes a conic mirror.

Additional Item 11

A microscope apparatus including a light source; an optical scanning unit configured to two-dimensionally scan light from the light source; an objective lens configured to irradiate a body lumen with the light scanned by the optical scanning unit and collect return light from the body lumen; and an optical detector configured to detect the return light collected by the objective lens and transmitted through the optical scanning unit, wherein objective lens includes a small-diameter end section that is inserted into the body lumen and a deflecting member that deflects the optical axis in a direction intersecting with the longitudinal axis so that the focal point is disposed outward of the small-diameter end section in the radial direction, and wherein the microscope apparatus includes focal-position adjusting means, disposed on the optical axis between the light source and the deflecting member, for displacing the position of the focal point in the radial direction.

Additional Item 12

The microscope apparatus according to Additional Item 11, wherein the focal-position adjusting means adjusts the focal point by changing the focal length of a lens.

Additional Item 13

The microscope apparatus according to Additional Item 11 or 12, further having a pinhole at an image-forming position conjugate with the focal point disposed upstream of the optical detector.

Additional Item 14

A microscope examination method including an inserting step of inserting a small-diameter end section of an objective lens whose focal point is disposed outward in the radial direction into a body lumen of a laboratory animal prepared so that a specific site generates light; a focal-position adjusting step of focusing at the light-generating site on the inner wall of the body lumen; and an image-acquiring step of acquiring an image of the in-focus light-generating site, wherein the focal-position adjusting step and the image-acquiring step are repeated while moving the small-diameter end section inside the body lumen.

Additional Item 15

The microscope examination method according to Additional Item 14 further including a step of moving the focal position in the radial direction of the small-diameter end section, carried out between the focal-position adjustment step and the image-acquisition step.

What is claimed is:

1. An examination method of carrying out in-vivo examination of a small laboratory animal using an examination apparatus configured to perform fluorescence examination and reflected-light examination, the method comprising:
   defining a reference position for setting an examination site in the small laboratory animal by carrying out reflected-light examination;
   switching from reflected-light examination to fluorescence examination;

designating a desired position of the examination site on an anatomical atlas of the small laboratory animal, the anatomical atlas being previously prepared based on in-vivo information data of the small laboratory animal;

measuring a distance from the reference position to the desired position of the examination site on the anatomical atlas of the small laboratory animal;

moving the examination site of the examination apparatus to the desired position based on the measured distance; and performing the fluorescence examination at the desired position of the examination site.

2. The examination method according to claim 1, wherein the defining of the reference position includes automatically detecting a focal position.

3. An examination apparatus comprising:

an orientation changing mechanism having a vertical-direction driving mechanism configured to move a focusing unit or a specimen table in an optical axis direction;

a control device including an anatomical atlas of a small laboratory animal that has been previously prepared based on in-vivo information data of the small laboratory animal, the control device being configured to:
  (i) measure a distance from a reference position to a desired position of an examination site on the anatomical atlas of the small laboratory animal, and
  (ii) control the vertical-direction driving mechanism, based on the measured distance, in order to move the examination site to the desired position; and a switching device configured to switch between reflected-light examination and fluorescence examination.

4. The examination apparatus according to claim 3, wherein the orientation changing mechanism includes:

a horizontal-direction driving mechanism configured to move the focusing unit or the specimen table in a direction orthogonal to the optical axis direction, and a rotational-direction driving mechanism configured to rotate the optical axis.

5. The examination apparatus according to claim 3 further including:

a focal-position automatic detection mechanism configured to automatically detect a focal position.

* * * * *